United States Patent [19]

Serrat

[11] Patent Number: 5,783,149
[45] Date of Patent: Jul. 21, 1998

[54] KIT FOR DETERMINATION OF RESIDUAL CHLORINE IN WATER WITH 3,3',5,5'-TETRAMETHYLBENZIDINE

[76] Inventor: Francisco Bosch Serrat, C/ Serpis, 15-5º-9ª , 46021 Valencia, Spain

[21] Appl. No.: 565,571

[22] Filed: Nov. 30, 1995

[30] Foreign Application Priority Data

Jul. 27, 1995 [ES] Spain ......................... 9501517

[51] Int. Cl.[6] ........................... G01N 33/84; G01N 21/77
[52] U.S. Cl. .......................... 422/61; 436/125; 436/39
[58] Field of Search .................... 436/125, 169, 436/164, 808, 810, 39; 422/61, 58

[56] References Cited

U.S. PATENT DOCUMENTS 3,992,158   11/1976   Przybylowicz et al. ............... 422/58
5,491,094    2/1996   Ramana et al. ....................... 436/125

OTHER PUBLICATIONS

F. Bosch Serrat, "Colorimetric Method for Determination of Chlorine with 3,3',5,5'-Tetramethylbenzidine" *Talanta*, vol. 41, No. 12, 2091-2094, 1994.

Tennant et al., "Classification according to chemical structure, mutagenicity to Salmonella and level of carcinogenicity of a further 39 chemicals tested for carcinogenicity by the U.S. National Toxicology Program", *Mutation Research*, 257 (1991) 209-227.

Standefer et al., "Use of Tetramethylbenzidine in Plasma Hemoglobin Assay", *Clin. Chem.* 23/4, 749-751 (1977).

Williams et al., "Substitution of tetramethylbenzidine for benzidine in cyanide analyses", *Clinica Chimica Acta*, 145 (1985) 113-118.

Attar et al., "Evaluation of a Polymer Film Impregnated with Reagents for the Detection and Determination of Chlorine in Air", *Arabian J. for Science and Engineering*, vol. 10, No. 2, 107-118, 1984.

Borzova et al., "Benzidine derivatives as reagents for the determination of chlorine", *Analytical Chemistry*, vol. 55 (1961) 25581.

American Public Health Association, "4500-Cl Chlorine (Residual)", *Standard Methods for the Examination of Water and Wastewater*, 18th Ed. 1992, 4-36.

*Primary Examiner*—Lyle A. Alexander
*Attorney, Agent, or Firm*—Heller Ehrman White & McAuliffe

[57] ABSTRACT

Colorimetric methods for determination of residual chlorine, free and combined, in water are described which comprise the use of 3,3',5,5'-tetramethylbenzidine (TMB), as well as methods and kits for determining chlorine in water by visual comparison which comprise, apart from TMB, a calibration scale. The basis for the preparation of one of the kits (or the kit described as an example) lies in the orange color that is produced by means of the reaction between chlorine and TMB, which permits a straightforward determination of residual chlorine by means of a simple visual comparison with a graduated, stable scale that is constituted either by solutions of Tropaeolin O of different concentrations or, alternatively, by a printed scale on plastic material or paper, by etching.

7 Claims, 3 Drawing Sheets

KIT FOR DETERMINATION OF RESIDUAL CHLORINE IN WATER WITH 3,3',5,5'-TETRAMETHYLBENZIDINE

FIELD OF THE INVENTION

The present invention relates to the determination in water of chlorine, either free or combined, by means of the use of 3,3',5,5'-tetramethylbenzidine. The invention provides colorimetric methods for the determination of chlorine in water, as well as methods and kits for chlorine determination in water based on visual comparison.

BACKGROUND OF THE INVENTION

Chlorine determination in water can be carried out by means of different techniques which include titration and potentiometry, although the most universally used technique is molecular absorption spectrophotometry, and particularly, colorimetry, due to its high sensitivity and rapidity. Until the seventies, o-tolidine (OT) was the most widely used chromogenic reagent to this end, but the discovery of its carcinogenic nature [J. Ashby and R. Tenant, "Definitive relationships among chemical structure, carcinogenicity and mutagenicity for 301 chemicals tested by the US NTP", Mutat. Res. 257, 229–306 (1991); American Public Health Association, American Water Works and Water Pollution Control Federation, "Standard Methods for the Examination of Water and Wastewater", 18th Ed., p.4.36 (1992)], occasioned a progressive decrease in its use, both in the USA and in most other countries, also being excluded in all issues after the 15th edition of the publication entitled "Standard Methods for the Examination of Water and Wastewater".

Nowadays, the two most frequently used reagents for the colorimetric determination of chlorine in water are N,N-diethyl-p-phenylenediamine (DPD) and syringaldazine, although in a very recent publication of the author of this invention [F. Bosch Serrat, "Colorimetric method for determination of chlorine with 3,3',5,5'-tetramethylbenzidine", Talanta, 41 2091–2094 (1994)] the use of 3,3',5,5'-tetramethylbenzidine (TMB) has been proposed as an adequate reagent for determining chlorine by means of a colorimetric method. This reagent, TMB, is not carcinogenic and has replaced benzidine, that does happen to be carcinogenic, in the analysis of hemoglobin and other Clinical Chemistry determinations [Standefer and Vanderjacht, "Use of tetramethylbenzidine in plasma hemoglobin assay", Clin. Chem., 23, 745–751 (1977); K. J. Williams, R. Rosenstein and R. O. Smith, "Substitution of tetramethylbenzidine for benzidine in cyanide analysis", Clin. Chim. Acta, 145, 113–118 (1985)]. TMB has also been tested with OT and ditizone to determine chlorine in air [K. M. Attar and P. W. West, "Evaluation of a polymer film impregnated with reagents for the detection and determination of chlorine in air", Arabian J. Sci. Eng., 10, 107 (1985)]. Furthermore, an unspecified form of tetramethylbenzidine has been studied along with other derivatives of benzidine to determine chlorine [L. D. Borzova, "Benzidine derivatives as reagents for the determination of chlorine", Uchenie Zapiski Saratov, 71, 239 (1959)].

The use of syringaldazine to determine chlorine in water presents some important drawbacks, such as the reduced stability of the reaction product, the fact that high concentrations of calcium and magnesium cause interferences in the determination of chlorine at high temperatures and the need of maintaining a strict pH control. Furthermore, total chlorine content in water cannot be determined with a method using syringaldazine as a reagent, and does not, therefore permit to determine the combined chlorine content present in analyzed water.

On the other hand, the use of DPD to determine chlorine in water also has numerous drawbacks. Its analytical and biological properties are inferior to those of 3,3',5,5'-tetramethylbenzidine (TMB), it is considered to be a toxic product, and it has a lower sensitivity as well as a low stability. Thus, its preservation requires the addition of ethylenediaminetetraacetic acid (EDTA) or other metal chelating agents.

As can be appreciated, there is a a continuous need for a method that determines residual chlorine content in water that overcomes the aforementioned inconveniences. In particular, it would be desirable to dispose of a method to determine chlorine content which is sensitive, which can be reproduced, which is simple, which does not require a rigorous pH control and which permits the determination of free as well as combined chlorine using a reagent which is not toxic, with which the metallic cations normally present in water such as, for example, Ca(II) and Mg(II), do not cause interferences in the determination of chlorine, which produces stable reaction products and presents an enhanced stability without having to use expensive treatments or maintenance with special reagents and devices.

This invention provides a solution to the posed problem, which comprises the use of reagent, 3,3',5,5'-tetramethylbenzidine (TMB) in a colorimetric method or a method of visual comparison to determine free or combined chlorine in water.

Therefore, it is an object of this invention to provide a colorimetric method to determine free and combined chlorine in water, and which comprises the use of 3,3',5,5'-tetramethylbenzidine (TMB) as a reagent.

A second object of this invention is to provide a visual comparison method to determine free and combined chlorine in water which comprises the use 3,3',5,5'-tetramethylbenzidine (TMB) as a reagent.

An additional object of this invention is to provide a kit to determine free and combined chlorine in water by means of a visual comparison method which comprises 3,3',5,5'-tetramethylbenzidine (TMB).

DETAILED DESCRIPTION OF THE INVENTION

Figure 1:
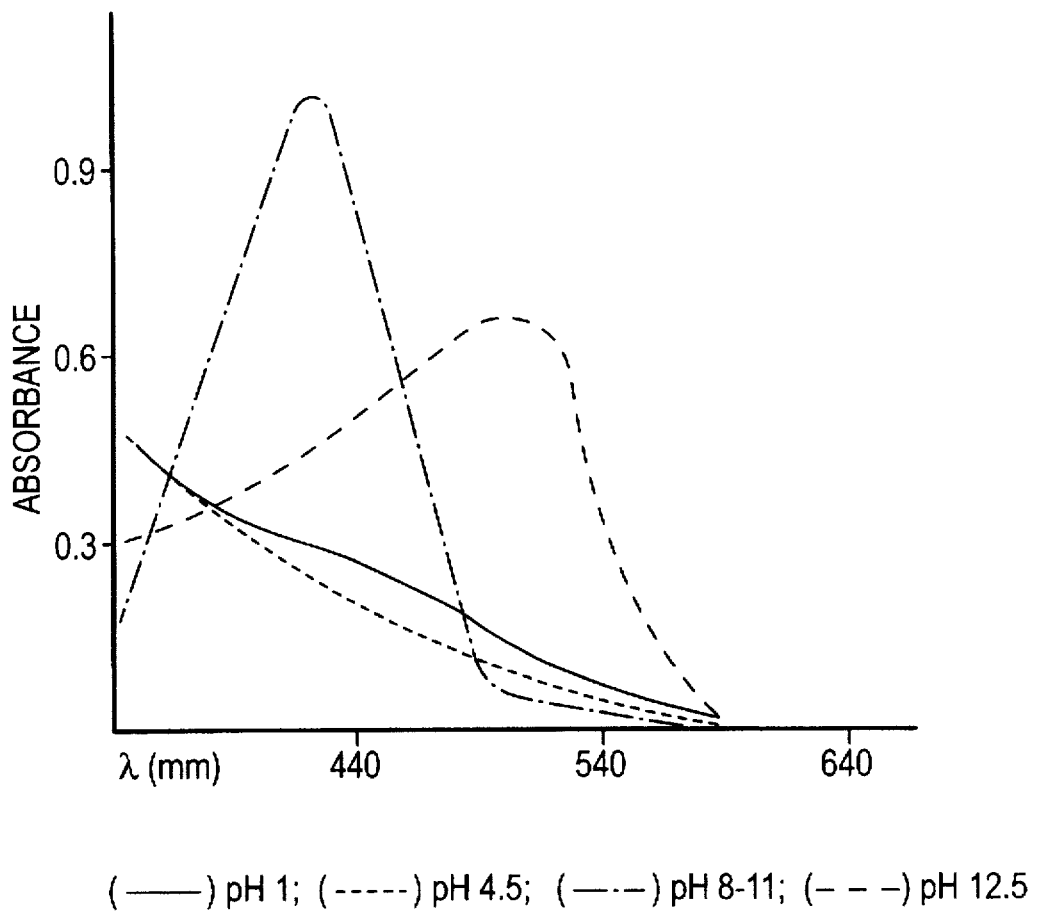
FIG. 1 shows the effect of pH on 10 mg of Tropaeolin O. (—) pH 1, ( - - - ) pH 4.5, (_._) pH 8–11 and (——) pH 12.5.

1. Colorimetric method for the determination of chlorine

In a first embodiment of this invention, a colorimetric method to determine free and combined chlorine in water is provided which comprises the use of 3,3',5,5'-tetramethylbenzidine (TMB) as a reagent.

The method for the determination of free chlorine includes the general following steps:

a) putting the solution of TMB into contact with the sample.

b) adding a solution of m-sodium arsenite to the mixture resulting from step a) before the lapse of 10 seconds.

c) measuring the absorbance of the resulting mixture and compare it with a blank sample treated in a similar manner, and d) determining the chlorine content from a calibration curve which contains known active chlorine concentrations.

Therefore, the embodiment of the above described method comprises the preparation of different solutions, such as the solution which comprises TMB, m-sodium arsenite in water and that of a reference calibration curve with known amounts of active chlorine.

TMB is scarcely soluble in water, even though its solubility increases with the addition of an inorganic acid up to a certain point where it begins to decrease due to the common-ion effect, but it is soluble in N,N-dimethylformamide (DMF) and in low molecular weight alcohols which have up to 5 carbon atoms. Therefore, the solution which comprises TMB is a solution of TMB in a solvent which comprises a) an organic solvent selected from the group formed by DMF and an alcohol with up to 5 carbon atoms and b) an aqueous solution of an acid in an adequate amount to give a pH equal to or lower than 2. In general, the organic solvent: aqueous solution ratio is between 1:2.3 and 1:4 (v/v). In a preferred embodiment of this invention, the solution which comprises TMB, is a solution of TMB in DMF and an aqueous solution of an inorganic acid, in a DMF:aqueous solution ratio of 1:3 (v/v), and the inorganic acid is o-phosphoric acid in a sufficient amount to give a pH that is less than 2. The o-phosphoric acid increases the stability of the TMB solution and prevents interferences due to Fe(III) in the determination of chlorine.

The solution of m-sodium arsenite can be prepared dissolving the adequate amount of solute in distilled water.

The chlorine reference solutions were prepared with sodium hipochlorite titrated with a reference solution of sodium thiosulphate. In general, chlorine solutions that allow to obtain a reference calibration curve which contains from 0.02 to 1 mg/liter of active chlorine or, alternatively, a reference calibration curve which contains from 0.04 to 1.5 mg/liter of active chlorine are sufficient.

In the determination of free chlorine, it is necessary that the addition of an m-sodium arsenite solution to the mixture resulting from the solution of TMB in DMF-water and the water sample be done in less than 10 seconds.

The absorbance must be read at 450 nm or at 650 nm. At an acid pH, the greater absorbance of the product of the reaction between TMB and chlorine [TMB-chlorine] takes place at a pH between 1 and 2 (see FIG. 2). At a pH less than 1, the color remains yellow, but its intensity decreases gradually with a decrease in pH. At a pH greater than 2, the color becomes darker progressively because the chlorine-TMB reaction changes to an isomeric form that has a bluish color that presents a maximum absorption at 650 nm. The yellow color appears again at a pH greater than 6. Therefore, for the colorimetric determination of residual chlorine in water according to the proposed method of this invention, the absorbance can be read at 450 nm., the pH of the reaction's medium having to be between 1 and 2 and the chlorine calibration curve must include the concentration range of 0.02 to 1 mg/liter of active chlorine. Alternatively, the absorbance can be read at 650 nm, the medium's pH having to be between 3.8 and 5.8, which can be achieved by means of an alkaline salt of phosphoric acid or by a suitable buffer, such as that formed by an acid and its conjugated base, for instance a carboxylic acid (acetic, malic and the like), and its conjugated base, and the chlorine calibration curve must include the concentration range between 0.04 and 1.5 mg/liter of active chlorine. In a preferred embodiment of this invention, a pH between 1 and 2 has been selected for the colorimetric determination of chlorine due to its greater sensitivity and a greater stability of the TMB-chlorine reaction product, which means the absorbance is read at 450 nm.

Since the determination of combined chlorine in water is not done in a direct manner, total and free chlorine content must be previously analyzed and, later on, subtract the amount of free chlorine from the amount of total chlorine. The determination of free chlorine can be done as explained above, while the determination of total chlorine is done by means of a method which comprises the following general steps:

a) putting a solution which comprises TMB into contact with the sample of water to be analyzed.

b) after 5 minutes, measuring the absorbance of the resulting mixture with reference to a blank mixture treated in a similar manner; and c) determining the chlorine content by means of a reference calibration curve which contains known concentrations of active chlorine.

The embodiment of the above described method for the total determination of chlorine comprises the preparation of a solution which comprises TMB and a reference calibration curve with known concentrations of active chlorine. Everything that was previously mentioned in relation to the solution which comprises TMB, with the calibration curve and the absorbance reading at 450 nm and 650 nm is applicable for the determination of total chlorine.

Once total and free chlorine are determined, the combined chlorine corresponds to the difference between total and free chlorine.

2. Method for the determination of chlorine by visual comparison

As was previously indicated, the determination of chlorine in water by means of the previously described colorimetric method can only be performed using very expensive equipment (spectrophotometer) and furthermore requires knowledge of the use of the instruments, the preparation of a calibration scale and other reagents, making the assistance of a laboratory technician necessary. However, the control of chlorine content in water is not exclusive of large drinking water suppliers, which are normally equipped with the aforementioned requirements, but in most cases said control must be effected in small water supplies, swimming pools and other places that do not dispose of the personnel or equipment to apply the colorimetric method.

This problem could be solved preparing a color calibration scale which is stable and that would permit the calculation, at any given time, of the chlorine concentration present in the sample, treated properly, by means of a visual comparison of its color with the calibration scale. This calibration scale should have an intensity and a hue that is exactly equal to those produced by specific analyte concentrations when they react with the chromogenic reagent. In general, the calibration scale of ideal color is prepared with the same compound to be determined in the sample. In this case, it would be a scale made with chlorine gas solutions, or better yet with sodium oxochlorate (I) (sodium hipochlorite), to which the reagent TMB is added, i.e., the one used in the colorimetric method. However, since the product of the reaction of chlorine with TMB is not very stable, a new scale would have to be prepared every two or three hours. Therefore, calibration solutions that are more stable during much longer periods of time must be found. This can be achieved with a product that provides the same color (hue and intensity) than that which is obtained by the mixture of certain analyte concentrations with the chromogenic reagent. In order to determine chlorine in water, this goal could be achieved using Cr (VI) solutions, but these compounds are toxic (and even considered carcinogenic by some experts), therefore other substances need be found that do not have such a serious inconvenience.

Alternatively, another way of effecting a color stable calibrating scale "in situ" is to photograph the Chlorine-TMB scale. This process does not lead to such accurate results as is the case when a tridimensional scale is used although it can present some advantages such as the straight-forwardness of the operation.

It has now been found that Tropaeolin O (CI #14270) may be used to prepare a stable color calibration curve that can be used to determine the chlorine content in water by visual comparison of the chlorine-TMB product formed with said calibration curve.

Therefore, this invention provides a method for visual comparison to determine free and combined chlorine in water, that comprises the use of 3,3',5,5'-tetramethylbenzidine (TMB) as a reagent as well as a stable color calibration curve, which in the preferred embodiment, comprises different solutions of Tropaeolin O.

The method to determine free and combined chlorine comprises the steps of:

a) putting into contact a solution that comprises TMB with the water sample to be analyzed.

b) determining the free chlorine concentration by visual comparison with the colors of a color calibration curve prepared with different Tropaeolin O concentrations before the lapse of 10 seconds.

c) determining the total chlorine concentration by visual comparison with the colors of a color calibration curve prepared with different Tropaeolin O concentrations after three minutes; and, if desired, d) determining the combined chlorine concentration by obtaining the difference between the total and the free chlorine concentrations.

The aforementioned described method comprises the preparation of a solution that comprises TMB and a color calibration curve prepared with different concentrations of Tropaeolin O.

The solution which comprises TMB is a solution of TMB in a solvent which comprises a) an organic solvent selected from the group formed by DMF and an alcohol with up to 5 carbon atoms and b) an aqueous solution of an inorganic acid in an adequate amount to give a pH equal to or less than 2. In general, the organic solvent: aqueous solution ratio is between 1:1.5 and 1:3 (v/v). In a preferred embodiment of this invention, the solution which comprises TMB, is a solution of TMB in isopropanol, or preferably in ethanol, and an aqueous solution of an inorganic acid in an alcohol: aqueous solution ratio of 1:2.3 (v/v) and the inorganic acid is hydrochloric acid in a sufficient amount to give a pH between 1 and 2. The solution which comprises TMB which can be used in this method by visual comparison presents some differences with respect to the solution which comprises TMB which is used in the colorimetric method. In this case, ethanol and hydrochloric acid have been substituted for DMF and o-phosphoric acid respectively. These modifications are aimed at increasing the stability of the reagent, which requires 30 to 40 % ethanol in order to maintain a dissolved concentration of 0.10% TMB in 0.5 mole/liter hydrochloric acid. However, the removal of o-phosphoric acid has the drawback that Fe(III) could interfere with the determination of chlorine in case its concentration were greater than 0.2 mg/ml, but this is very unlikely in drinking water. The solution which comprises TMB prepared in ethanol (30%) (v/v) and aqueous solution of hydrochloric acid (0.5 moles/liter), at room temperature and kept away from sun light, is stable for at least 7 months.

The Tropaeolin O (CI #14270) base calibration scale comprise different solutions of Tropaeolin O in a solvent comprising glycerol and an aqueous solution of an inorganic base in an adequate amount to give a pH equal to or greater than 8, preferably between 9 and 11. Generally, the glycerol:basic aqueous solution ratio is comprised between 1:1 and 1:9 (v/v). The glycerol not only decreases the volatility of solvent and the possibility of absorption of the dye in the container walls, but also affects the stability of said solutions. The basic aqueous solution can comprise any inorganic base, providing the adequate pH and that does not interfere in the determination of chlorine, preferably, sodium bicarbonate and sodium hydroxyde.

The equivalence between the concentration of Tropaeolin O with the concentration of chlorine is shown in Table 1.

TABLE 1

| Equivalence [Tropaeoline O] versus [chlorine] | | | |
|---|---|---|---|
| Tropaeolin O mg/l | Chlorine mg/l | Tropaeolin O mg/l | Chlorine mg/l |
| 0.52 | 0.05 | 6.30 | 0.60 |
| 1.05 | 0.10 | 8.40 | 0.80 |
| 2.10 | 0.20 | 10.50 | 1.00 |
| 3.15 | 0.30 | 15.75 | 1.50 |
| 4.20 | 0.40 | 21.00 | 2.00 |

Additionally, the invention provides kits for determining free and combined chlorine in water by means of a method that of visual comparison which comprises 3,3',5,5'-tetramethylbenzidine (TMB). For example, one of the kits comprises:

a) containers and measuring devices b) contents (a reagent solution of TMB and different Tropaeolin O solutions); and c) instructions for their use In a preferred and particular embodiment, the containers of such a kit are 11 flasks of transparent glass of about 12 ml volume and a water tight screw-on cap. Ten of the flasks are intended to contain the calibration curve solutions, whereas the remaining one is used to place the water sample (10 ml) with some TMB reagent drops, usually 8 to 10 drops. The kit also includes a plastic dropping tube of a volume of approximately 16 ml which contains the TMB reagent solution, and there is also a plastic graduated test-tube to measure the water sample. All these devices, as well as the instructions, can be placed in a box or case with appropriate housings.

Alternatively, and as a substitute for a the three dimensional calibration scale, a scale printed on a plastic material or paper can be obtained by means of a photographic or etching process.

The following examples serve to illustrate specific embodiments of this invention.

EXAMPLE 1

Colorimetric determination of chlorine

This assay was performed to determine total (free and combined) chlorine contained in drinking water from Burjassot (Valencia) using samples obtained in three different days.

1.1 Apparatus

The spectrum measurements as well as the absorbance readings were obtained using a double beam Shimadzu UV-240 spectrophotometer using a glass cell of 1 cm.

The pH meter used was a Crison 2000 model.

1.2 Preparation of reagents

The reference chlorine solutions were prepared with sodium hipochlorite titrated with a reference sodium thiosulphate solution. Reference chlorine solutions containing from 0.02 to 1 mg/liter of active chlorine were prepared.

A solution of TMB in N,N-dimethylformamide (DMF)-water was prepared dissolving 0.100 gr of TMB in 25 ml of DMF and later on diluting with 50 ml of o-phosphoric acid and 25 ml of distilled water. In addition, a solution of sodium m-arsenite (5 gr/liter) in distilled water was prepared.

All reagents were of analytical grade.

1.3 Determination of free chlorine

Two ml of the TMB in DMF-water solution were placed in an Erlenmeyer flask, 50 ml of the water sample to be analyzed were suddenly added and before 10 seconds elapsed, 2 ml of the sodium m-arsenite solution were also added and the absorbance at 450 nm was measured with reference to a blank treated in a similar manner. The chlorine content was determined from a reference calibration curve that contained 0.02 to 1 mg/liter of active chlorine. The obtained results are shown in Table 2.

TABLE 2

| Determination of free chlorine | | |
|---|---|---|
| Sample | mg/liter | RSD (%) |
| 1 | 0.62 | 0.7 |
| 2 | 0.54 | 1.0 |
| 3 | 0.52 | 1.0 |

The results from the free chlorine determination (Table 2) obtained with the method of this invention are in accordance with the results obtained by the colorimetric method that uses syringaldazine as a reagent [F. Bosch Serrat, cited supra]

1.4 Determination of total chlorine (free and combined)

Two ml of the TMB solution in DMF-water were placed in an Erlenmeyer flask, 50 ml of the water sample to be analyzed were added and thoroughly mixed. The absorbance at 450 nm with reference to a blank treated in a similar manner was measured after 5 minutes. The chlorine content was determined from a reference calibration curve which contained 0.02 to 1 mg/liter of active chlorine. The content of combined chlorine was calculated from the difference between total and free chlorine. The results are shown in Table 3.

TABLE 3

| Determination of total chlorine (free and combined) | | |
|---|---|---|
| Sample | Total (mg/liter) | Free chlorine (%) |
| 1 | 0.45 | 87.1 |
| 2 | 0.52 | 86.7 |
| 3 | 0.41 | 87.3 |

The results of the total chlorine determination (Table 3) obtained with the method of this invention are in agreement with the results obtained with a colorimetric method using o-tolidine as a reagent [F. Bosch Serrat, cited supra].

1.5 Comments

The obtained results showed that the free chlorine colorimetric determination in water using TMB can be performed with an accuracy very similar to that achieved by using syringaldazine, even though the sensitivity of the method is much greater with TMB. In addition, the method of the invention presents the advantages that the reaction product has a high stability, there are no interferences with high calcium and magnesium concentrations and a rigorous pH control is not required. Furthermore, unlike the method which use syringaldazine, it is possible to determine with TMB not only the content of free chlorine but also the total chlorine. [F. Bosch Serrat, cited supra].

EXAMPLE 2

Chlorine determination by visual comparison

This test was performed in order to determine total, chlorine, free and combined, contained in drinking water by visual comparison.

2.1 Preparation of reagents

For the preparation of the TMB reagent, 100 mg of TMB were dissolved in 30 ml of ethanol, then 50 ml of 1 mole/liter hydrochloric acid were added and distilled water was added to the 100 ml mark.

In order to prepare the calibration scale, 105 mg of Tropaeolin O (CI#14270) were dissolved in distilled water and filled up to 1 liter. From this solution, 0.5; 1; 2; 3; 4; 5; 6; 8; 10; 15 and 20 ml samples were taken and distilled water was added to them to complete 25 ml, together with 50 ml of glycerol, 12 ml of 0.5 mole/liter sodium bicarbonate and 8 ml of 0.5 mole/liter sodium hydroxyde. The resulting mixture was homogenized and filled with distilled water up to the 100 ml mark. From each one of these solutions, 10–11 ml are placed in the kit flasks.

2.2 Chlorine determination 8 to 10 drops of the TMB reagent are added, and then 10 ml of sample water to be analyzed are placed in the empty flask, the flask is closed, it is shaken and the chlorine concentration is calculated by comparison with the Tropaeolin O color scale. A comparison before 10 seconds gives the free chlorine, whereas the comparison performed after 3 minutes indicates the total chlorine.

EXAMPLE 3

Effect of pH on the color of Tropaeolin O solutions

The effect of pH on the color of Tropaeolin O solutions is shown in FIG. 1. At acid pH, Tropaeolin O solutions are yellow and their absorption spectrum does not present a maximum between 400 and 700 nm, in contrast to the reaction product of Chlorine with TMB, which is orange in color and has a maximum at 450 nm. As the pH of Tropaeolin O solutions increases they acquire an orangish hue and between pH 8 and 11, their absorption spectrum presents a unique maximum at 431 nm and usually the color of the product of the reaction of chlorine with TMB (at pH 1–2) and that one of Tropaeolin O are practically equal. At higher pH than 11, the color becomes progressively darker and the possibility of chlorine determination by visual comparison of colors of the sample-TMB solutions disappears against Tropaeoline O solutions.

Figure 2:
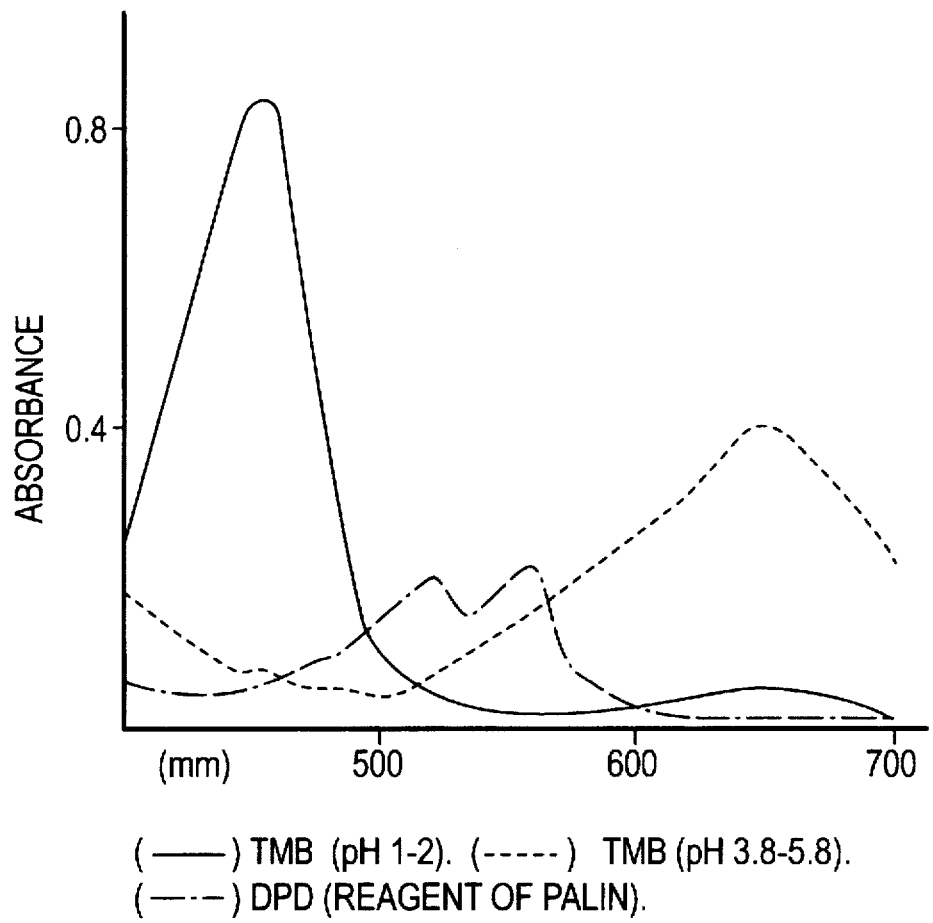
FIG. 2 shows the TMB and DPD spectrum with a reference chlorine solution with a concentration of 0.8 mg/liter. (—) TMB (pH 1–2), ( - - - ) TMB (pH 3.8–5.8) and (—.—) DPD.

The color of the reaction product of chlorine-TMB is also influenced by the pH (see FIG. 2, wherein the spectrum of the DPD-chlorine reaction product is also included). The yellow-orangish color with a pH lower than 2 first changes to green and later to blue between pH 4 and 6. At a pH greater than 6 a yellow color appears whose stability is much lower than the reaction product at pH 1–2. In view of the pH effect on the color and stability of the reaction product, one can deduce the possibility of determining colorimetrically the residual chlorine at a pH between 4 and 6, using a calibration scale of 0.04 to 1.5 mg/liter of chlorine, measuring the absorbance at 650 nm or comparing the color of the sample with those of the etched or photographed scale, even though this option has the disadvantage that it is less sensitive than the chlorine determination at a pH between 1 and 2.

Figure 3:
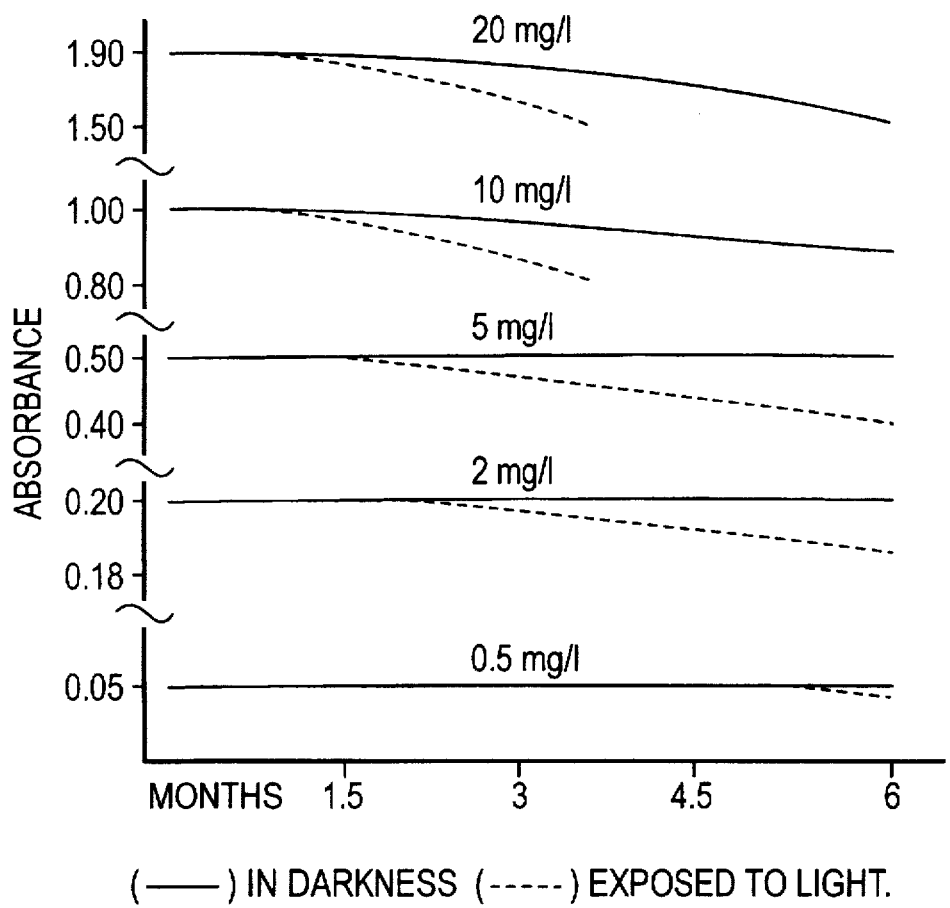
FIG. 3 shows the effect of time and light on the stability of the Tropaeolin O scale in darkness (—) and exposed to light ( - - - ).

EXAMPLE 4
Effects of time, light and glycerol on the stability of the calibrating scale The effects of light and time on the calibration scale are represented on FIG. 3. The Tropaeolin O solutions are not very much affected by direct sun light that is filtered through ordinary glass due to the fact that exposure to it for one month does not change the absorbance at 431 nm of the calibration scale solutions.

Therefore, it can be assumed that short exposures to sun light will have no effect on the stability of the scale.

The elapsed time influences more on high concentrations of Tropaeolin O more (10.5–21 mg/liter). The solutions of 0.52, 1.05 and 2.1 mg/liter of Tropaeolin O are stable at least for 6 months, while that of 5.2 mg/liter Tropaeolin O solution (corresponding to 0.5 mg/liter of chlorine at 430 nm) suffers a decrease of absorbance of approximately 2% and 6% after 3 and 6 months respectively, that is not relevant because it cannot be detected visually. Tropaeolin O concentrations from 10.5 to 21 mg/liter (1–2 mg/liter chlorine) decrease their color intensity from 5 to 10% in 2 months. Yet fortunately, the concentrations of 1 or more mg/liter of chlorine in water are by no means frequent.

The use of glycerol (1,2,3-propanotriol) in the preparation of Tropaeolin O solutions not only diminishes solvent volatility and the possibility of absortion of dye on the container walls, but also has an influence on the stability of such solutions. Ratios of 50/50 (v/v) glycerol/water suffer a 10% decrease in absorbance 10% lower than Tropaeolin O solutions prepared with 10–20% (v/v) of glycerol.

I claim:

1. A kit for the determination of chlorine in water comprising:

a) a solution of 3,3',5,5'-tetramethylbenzidine (TMB) at a pH from about 1 to 2, and b) means for determining the amount of the TMB-Cl reaction product formed.

2. A kit according to claim 1, wherein said means for determining the amount of the TMB-Cl reaction product formed comprises several Tropaeolin O solutions, with different concentrations, corresponding to predetermined chlorine concentrations, in a solvent consisting of glycerol and an aqueous solution of an inorganic base.

3. A kit of claim 1, wherein said means for determining the amount of TMB-Cl reaction product formed is a calibration scale comprising a printed scale on plastic material or paper obtained by means of a photographic or etching process.

4. A kit according to claim 1, wherein the solution of TMB comprises TMB in a medium formed by an organic solvent and an aqueous solution of an inorganic acid.

5. A kit according to claim 4, wherein said organic solvent is selected from the group consisting of N,N-dimethylformamide (DMF) and an alcohol of up to 5 carbon atoms.

6. A kit according to claim 4, wherein said organic solvent is ethanol.

7. A kit according to claim 4, wherein said inorganic acid is selected between o-phosphoric acid and hydrochloric acid.

* * * * *